(12) United States Patent
Colman et al.

(10) Patent No.: US 7,500,483 B2
(45) Date of Patent: Mar. 10, 2009

(54) NEONATAL AIRWAY ADAPTOR

(75) Inventors: Lewis Colman, Jerusalem (IL);
Gershon Levitsky, Jerusalem (IL)

(73) Assignee: Oridion Medical (1987) Ltd., Jerusalem (IL)

( * ) Notice: Subject to any disclaimer, the term of this patent is extended or adjusted under 35 U.S.C. 154(b) by 588 days.

(21) Appl. No.: 11/126,066

(22) Filed: May 9, 2005

(65) Prior Publication Data

US 2005/0279362 A1   Dec. 22, 2005

Related U.S. Application Data

(63) Continuation of application No. 10/009,847, filed as application No. PCT/IL00/00336 on Jun. 7, 2000, now Pat. No. 6,926,005.

(30) Foreign Application Priority Data

Jun. 8, 1999    (IL) .................................... 130369

(51) Int. Cl.
*A61M 16/00* (2006.01)
*A61M 16/20* (2006.01)

(52) U.S. Cl. .................... 128/207.14; 128/207.15; 128/207.16; 128/204.18; 128/911; 128/912

(58) Field of Classification Search ............ 128/200.26, 128/202.27, 207.14, 207.15, 207.16, 207.17, 128/911, 912; 600/529, 531, 543
See application file for complete search history.

(56) References Cited

U.S. PATENT DOCUMENTS

| | | | |
|---|---|---|---|
| 3,461,877 A | 8/1969 | Morch | |
| 4,052,990 A | 10/1977 | Dodgson | |
| 4,221,130 A | 9/1980 | Burrows | |
| 4,558,708 A | 12/1985 | Labuda et al. | |
| 4,909,248 A * | 3/1990 | McLennan Anderson | 128/207.14 |
| 5,101,817 A | 4/1992 | Etter | |
| 5,107,829 A * | 4/1992 | Lambert | 128/202.16 |
| 5,178,138 A | 1/1993 | Walstrom et al. | |
| 5,251,616 A * | 10/1993 | Desch | 128/200.26 |
| 5,355,876 A * | 10/1994 | Brodsky et al. | 128/202.27 |

(Continued)

FOREIGN PATENT DOCUMENTS

DE   298 11 374 U1   10/1998

(Continued)

*Primary Examiner*—Justine R Yu
*Assistant Examiner*—Clinton Ostrup
(74) *Attorney, Agent, or Firm*—EMPK & Shiloh, LLP

(57) ABSTRACT

This invention is a neonatal airway adapter (10) with a sliding internal passage (54), which virtually eliminates void volumes (112) within the bore (76) of the airways, such that mixing of the exhales pages with void gases is reduced, and the waveform of the breath is maintained without undue distortion. Furthermore, the virtual elimination of void volumes reduces the level of re-breathing. The neonatal airway adapter connects to endotracheal tube adapters is such a way as to nullify the effect of the differing internal diameters (20) and internal lengths which are used in ET adapters currently available. The cross section of the internal bore of the airway through which the breath flows from the ET adapter to the connector of the ventilator is maintained almost constant, especially in the region of the gas sampling point (66), to ensure that reasonable conditions of laminar flow, and accurate sampling are maintained.

6 Claims, 3 Drawing Sheets

U.S. PATENT DOCUMENTS

| | | |
|---|---|---|
| 5,636,625 A | 6/1997 | Miyagi et al. |
| 5,642,726 A | 7/1997 | Owens et al. |
| 5,789,660 A | 8/1998 | Kofoed et al. |
| 5,857,461 A | 1/1999 | Levitsky et al. |
| 6,026,810 A | 2/2000 | Baird |
| 6,142,148 A * | 11/2000 | Weckstrom et al. .... 128/204.22 |
| 6,437,316 B1 * | 8/2002 | Colman et al. ........... 250/222.1 |
| 6,516,803 B1 | 2/2003 | Enzinger |
| 6,926,005 B1 * | 8/2005 | Colman et al. ......... 128/207.14 |
| 2004/0069307 A1 * | 4/2004 | Rich et al. ............. 128/207.14 |

FOREIGN PATENT DOCUMENTS

| | | |
|---|---|---|
| DE | 198 38 370 C1 | 9/1999 |
| EP | 0 827 713 A1 | 3/1998 |
| FR | 2 692 154 | 12/1993 |
| WO | WO-93/25261 | 12/1993 |
| WO | WO 00/74756 A1 * | 12/2000 |

* cited by examiner

NEONATAL AIRWAY ADAPTOR

The present application is a continuation of U.S. application Ser. No. 10/009,847, which was filed in the U.S. Patent and Trademark Office on Apr. 8, 2002 now U.S. Pat. No. 6,926,005, as a National Phase of PCT application PCT/IL00/00336 filed Jun. 7, 2000, which claims the benefit under 35 U.S.C. 119(a) from Israeli Application No. 130369, which was filed in the Israeli Patent and Trademark Office on Jun. 8, 1999. The disclosures of all these applications, including all appendixes thereof, are incorporated herein by reference.

FIELD OF THE INVENTION

The present invention relates in general to the field of airway adapters for the connection of an endotracheal tube to ventilation apparatus, particularly for use with neonatal patients.

BACKGROUND OF THE INVENTION

Airway adapters are generally used with patients being given respiratory assistance, such as patients under anesthesia, or patients on life support systems, to connect between the endotracheal tube (ET tube) and the ventilating tube of the breathing apparatus. These tubes convey breathing gases to the patient and exhaled breath away from the patient. The airway adapter is in the form of a short connector of tubular shape, and is required to make a connection between the generally very different cross sections of these two tubes. The airway adapter connected directly to the endotracheal tube is known as the ET adapter. Airway adapters also have the function of providing a demountable joint in the ventilation path, for the insertion of other tubes into the patient's lungs, and for the dispensing of medication into the pulmonary areas. This is necessary since it may be difficult to remove the ET itself from its connector port, without disturbing the patient or his treatment.

A non-invasive indication of the patient's respiratory condition can be obtained by the analysis of the exhaled breath gases. The measurement of the dynamic carbon dioxide content of the exhaled breath is known as capnography. Airway adapters with sampling ports are used to collect gas samples from the exhaled breath of patients for analysis. ET adapters are also available with a small-bore port extending into the wall of the gas flow path, to collect samples of the gas flowing in the airway, for gas analysis. Since, however, capnography measurements are generally not performed on a continuous basis, and the use of a sampling ET adapter would thus necessitate the sealing of the sampling port for most of the time, and the potential danger of bacterial growth in any debris lodged in the blind sampling tube, such sampling ET adapters are not generally used, a priori, for intubated neonatals. Furthermore, the termination of the sampling ports in the wall of the ET adapter airway is likely to cause the ingestion of secretions and liquids into the gas analyzer through the sampling line, especially during pulmonary suction procedures, when liquids could be sucked straight from the lungs into the sampling port opening. To avoid this problem, ET adapters are available with a sampling port extending into the center of the bore. This, however, interferes with the insertion of other tubes and apparatus down the ET tube.

For all of the above reasons, a generally used procedure with neonatals is not to use a sampling ET adapter on commencement of intubation, but to add an airway adapter with sampling port later, if and when required.

The accuracy of the capnographic measurement depends on the maintenance of a smooth laminar flow of the patient's breath through the airway adapter, so as to maintain the waveform of the exhaled breath. The waveform, which is the time varying level of carbon dioxide in the patient's breath, contains detail which can change with a response time of 10 to 100 msec. The exact form of the waveform, including these fast variations, provides information about the patient's respiratory state. Internal mixing of the gases or alterations in the waveform reduce the accuracy of the capnographic measurement by slowing down the response time, and hence reduce the amount or accuracy of diagnostic information extractable from the capnograph.

Airway components are typically made as plastic injection moldings, to enable production costs to be kept low. In order to ensure gas tight joins, components to be connected are generally produced with slight tapers, such that one component fits snugly into the other. Because of the comparatively wide manufacturing tolerances of such plastic parts, there is a wide spread in the closed dimensions of a joined pair of matching parts. Thus for instance, a loose-fitting ET adapter/ventilation tube connector pair will seal when one part is pushed much further into the other, than a tight-fitting pair. As a consequence of this, the amount of void volume (also known as dead space) produced in such a connection is very variable, and for a tight fitting pair, could be very considerable. The airway adapter should have minimal added void volume, both to reduce the effects of gas mixing, which would adversely affect the integrity of the waveform, and to reduce the anatomical dead space, which results in rebreathing.

Furthermore, the exhaled breath of patients always contains condensable water vapor, and can also contain a significant level of liquid or solid secretions such as mucous secretions and saliva. Such liquids can block or partially block the sampling line, causing a reduction in the pressure of the gases passing through the airway adapter into the gas analyzer. This pressure drop can cause alterations in the waveform, mixing of the gas, and alterations in the gas concentration, all of which reduce the accuracy of the gas analysis. The need for accurate analysis of the gas therefore dictates efficient separation of the gas from accompanying liquids or solids, while maintaining smooth laminar flow, and without the production of a substantial pressure drop or alteration in the gas waveform.

A number of novel designs for such airway adapters have been presented in U.S. Pat. No. 5,857,461, entitled "Multiple Channel Sample Port" to the present Applicants, and hereby incorporated in its entirety by reference. Furthermore, in the Background section of that patent are mentioned a number of other patents which describe airway adapters of other designs. However, none of the airway adapters described therein are satisfactory for use with neonatals. A major problem with neonatal patients is the very small flow involved. Thus for instance, a neonatal may typically exhale breaths of only 4 cc., while the volume of a standard adult airway adapter is 6 to 8 cc. This means that even a very small void volume can cause significant mixing of the neonatal's exhaled breaths, and inaccurate capnographic results. Furthermore, the fast breathing rate of neonatals makes a fast response time even more critical than for other patients. In addition, it is impractical to disconnect the ET tube of an intubated neonatal in order to change the ET adapter to fit the sampling device to be used. Finally, closed circuit systems which include suction are widely used, and it is impractical to break such circuits in order to insert and remove capnographic adapters as needed.

There therefore exists a serious need for a sampling airway adapter, especially for use with neonatal patients, which overcomes the drawbacks and disadvantages which hitherto available adapters show when used with such patients.

The disclosures of all publications mentioned in this section and in the other sections of the specification, are hereby incorporated by reference, each in its entirety.

SUMMARY OF THE INVENTION

The present invention seeks to provide a new airway adapter of novel construction which enables its use with neonatal patients without detracting significantly from the accuracy of capnographic measurements being performed on the patient, and without interfering unduly with the ventilation of the patient.

There is thus provided in accordance with a preferred embodiment of the present invention, a neonatal airway adapter which virtually eliminates void volumes (dead space) within the bore of the airways, such that mixing of the exhaled gases with void gases is reduced to minimal levels, and the waveform of the breath is maintained without unnecessary distortion. Furthermore, the virtual elimination of void volumes is clinically beneficial to the patient, since void volumes prevent the dispersion of the exhaled carbon dioxide, and cause a higher level of rebreathing. For this reason too, the neonatal airway adapter according to the present invention adds a minimal length to the airway circuit, in a situation where any excess length makes the dispersion of exhaled carbon dioxide more difficult.

Furthermore, according to a further preferred embodiment of the present invention, the neonatal airway adapter connects to endotracheal tube adapters in such a way as to nullify the effect of the differing internal diameters and internal lengths which are used in ET adapters currently available.

In addition, according to a further preferred embodiment of the present invention, the cross-section of the internal bore of the airway through which the breath flows from the ET adapter to the connector of the ventilator is maintained almost constant, especially in the region of the gas sampling point, to ensure that reasonable conditions of laminar flow are maintained.

The additional response time added to the response time of the rest of the airway system by a neonatal airway adapter according to preferred embodiments of the present invention, is minimal, such that the accuracy of capnographic measurements being performed on the neonatal patient are virtually unaffected.

In order to minimize the ingression of secreted liquids or breath-borne moisture into the gas analyzer sampling line, according to a preferred embodiment of the present invention, the gas sampling point is located in the center of the airway bore, away from the walls, in such a position as to reduce the liquid entrance level by a significant factor compared with prior art airway adapters. This factor too assists in avoiding clogging of the sample line, which would affect the faithfulness of waveform transmission, and by reducing the initial moisture level of the analyzed gas, also improves analysis accuracy.

Another advantage of an airway adapter according to a preferred embodiment of the present invention, is that since it has a minimally short length, it does not interfere unduly with the ventilation of the patient, and is not unduly cumbersome. Thus, even when capnographic measurements are not required, it can be left in circuit without affecting the well-being or treatment of the patient, and likewise, when used with closed circuit suction systems. This is in contrast with prior art adapters, which often need to be removed from circuit when not in use, this being a complex action with an intubated neonatal. Furthermore, the risk of infection is reduced if the breathing circuit is not disturbed.

In accordance with yet another preferred embodiment of the present invention, there is provided an airway adapter consisting of a first end section for connecting to an endotracheal tube adapter having an inner bore, the first end section having a passage formed therein, a second end section for connecting to a ventilating tube connector, the second end section being in fluid communication with the first end section, a sampling port intermediate the end sections in fluid communication with the first end section, and a tubular insert with an internal bore, which slides axially in the passage.

There is further provided in accordance with yet another preferred embodiment of the present invention an airway adapter as described above and wherein the internal diameter of the internal bore of the insert gradually increases towards an end of the insert near the sampling port, such that the internal diameter of the internal bore becomes essentially equal to the internal diameter of the passage.

In accordance with still another preferred embodiment of the present invention, there is provided an airway adapter as described above and wherein the insert has a projection adapted to abut against a portion of the first end section, which provides an axial motion limit into the passage, or wherein the projection consists of a lip on the external wall of the insert.

In accordance with a further preferred embodiment of the present invention, there is also provided an airway adapter as described above and wherein an outer wall of the insert has a surface profile such that the friction between the insert and the passage prevents the insert from sliding freely within the passage.

There is further provided in accordance with still another preferred embodiment of the present invention an airway adapter as described above and wherein the internal bore of the insert at an end of the insert distant from the sampling port, has an internal diameter essentially equal to the internal diameter of the inner bore of the endotracheal tube adapter, thereby providing a virtually smooth-walled passage from the inner bore of the endotracheal tube adapter to the internal bore of the insert.

There is provided in accordance with yet a further preferred embodiment of the present invention an airway adapter as described above and wherein the end of the insert distant from the sampling port abuts against the end of the inner bore of the endotracheal tube passage, thereby resulting in virtual elimination of void volume between the inner bore of the endotracheal tube adapter and the internal bore of the insert.

There is even further provided in accordance with a preferred embodiment of the present invention an airway adapter as described above and wherein the virtually smooth-walled passage is operative to allow a breath waveform to pass essentially without affecting its waveform.

Furthermore, in accordance with yet another preferred embodiment of the present invention, there is provided an airway adapter as described above and wherein the virtual elimination of void volume is operative to allow a breath waveform to pass essentially without affecting its waveform.

There is also provided in accordance with a further preferred embodiment of the present invention an airway adapter as described above and wherein the sampling port has openings located radially distant from the side walls of the passage.

In accordance with yet another preferred embodiment of the present invention, there is provided an airway adapter consisting of a first end section for connecting to an endotracheal tube adapter having an inner bore, the first end section having a passage formed therein, the passage having an outer wall, a second end section for connecting to a ventilating tube connector, the second end section being in fluid communication with the first end section, a sampling port intermediate the end sections in fluid communication with the first end section, and a tubular sleeve with an internal bore, which slides axially on the outer wall of the passage.

There is further provided in accordance with yet another preferred embodiment of the present invention an airway adapter as described above and wherein an internal diameter of the inner passage increases towards an end of the passage near the sampling port.

There is further provided in accordance with yet another preferred embodiment of the present invention an airway adapter as described above and also consisting of a spring operative to push the sleeve axially in a direction away from the sampling port.

In accordance with still another preferred embodiment of the present invention, there is provided an airway adapter as described above and wherein the internal bore of the inner passage has an internal diameter essentially equal to the internal diameter of the inner bore of the endotracheal tube adapter, thereby providing a reasonably smooth-walled passage from the inner bore of the endotracheal tube adapter to the internal bore of the inner passage.

There is further provided in accordance with still another preferred embodiment of the present invention an airway adapter as described above and wherein the end of the sleeve distant from the sampling port abuts against the end of the inner bore of the endotracheal tube passage, thereby resulting in virtual elimination of void volume between the inner bore of the endotracheal tube adapter and the internal bore of the sleeve.

In accordance with a further preferred embodiment of the present invention, there is also provided an airway adapter as described above and wherein the virtually smooth-walled passage is operative to allow a breath waveform to pass essentially without affecting its waveform or wherein the virtual elimination of void volume is operative to allow a breath waveform to pass essentially without affecting its waveform.

There is provided in accordance with yet a further preferred embodiment of the present invention an airway adapter as described above and wherein the virtual elimination of void volume between the inner bore of the endotracheal tube adapter and the internal bore of the insert is effective independently of the relative position in which the endotracheal tube adapter and the airway adapter are mated.

Furthermore, in accordance with yet another preferred embodiment of the present invention, there is provided an airway adapter as described above and wherein the virtual elimination of void volume between the inner bore of the endotracheal tube adapter and the internal bore of the sleeve is effective independently of the relative position in which the endotracheal tube adapter and the airway adapter are mated.

There is also provided in accordance with a further preferred embodiment of the present invention an airway adapter as described above and wherein an end of the insert distant from the sampling port is constructed of a pliant material.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
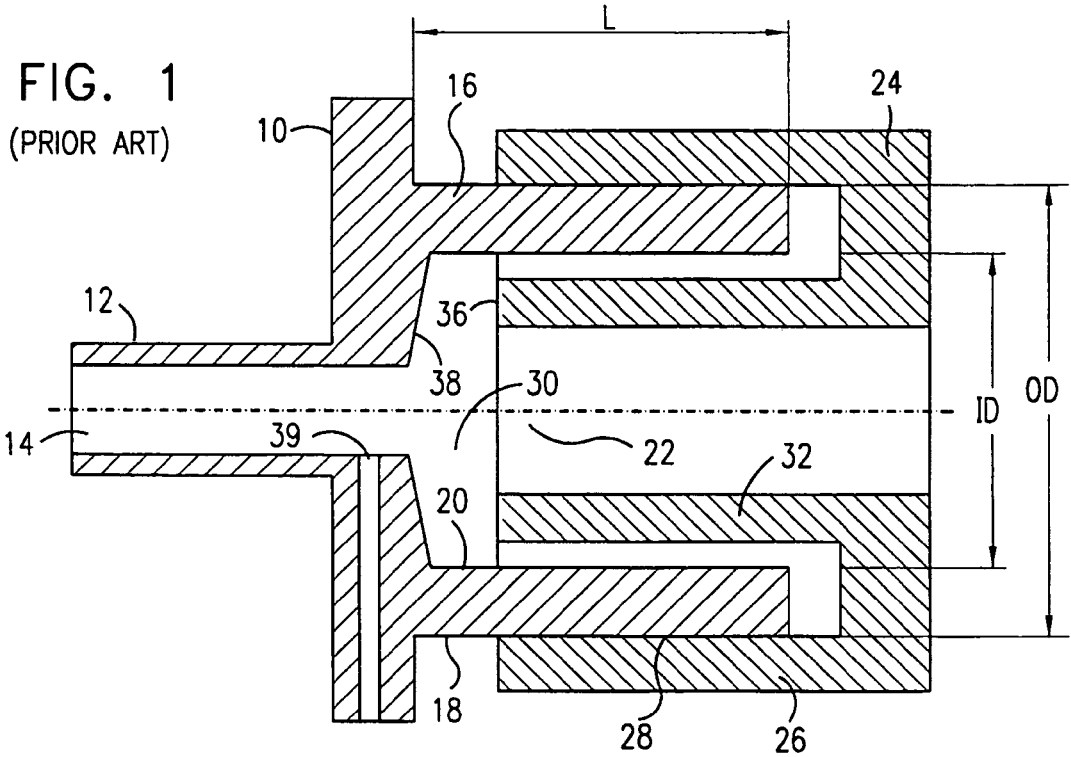
FIG. 1 is a cross-sectional view of a prior art airway connection made between an endotracheal tube (ET) adapter and a ventilation tube connector.

Reference is now made to FIG. 1, which is a cross-sectional view of a prior art airway connection made between an endotracheal tube (ET) adapter 10 and a ventilation tube connector 24, typically attached at its remote end to breathing apparatus. One end of the ET adapter 10 is formed into a narrow tubular section 12, having a wall and a central bore 14, over which the end of ET tube itself is fitted. Neonatal ET tubes are available in sizes ranging from 2.5 to 4 mm. The exhaled and breathing support gases are passed from and to the patient through this bore 14. The ET tube is attached over this tubular section which generally has an inner diameter (ID) of 3.5 mm, this being suitable for most neonatal ET tubes. This ET adapter can also be provided with a gas monitoring port, terminating at a hole 39 in the ET adapter wall.

At the other end of the ET adapter, there is a wide bore tubular opening having a wall 16 and a central bore 22 of similar size to that of the ventilation tube. The ventilation tube has to be of wide bore, since ventilation tubes are typically 2 meters long, and a narrow bore, like that of the ET tube, would severely limit the breathing gas conduction. The outside diameter (OD) 18 of the tubular opening is of a generally standard size, whereas the inside diameter (ID) 20 and the length L are not of universally standardized size. The ventilation tube connector 24 is attached to the ET adapter by sliding the outer wall 26 of the ventilation tube connector over the wall 16 of the wide bore tubular opening of the ET adapter. The outer wall 16 of the wide bore tubular opening of the ET adapter has a very slight conical taper, narrowing towards the ventilation tube end, and the inner surface 28 of the outer wall 26 of the ventilation tube connector has a matching conical taper, widening towards the ET adapter end, such that when assembled, the two parts form a good gas-tight connection.

However, when the ET adapter 10 is connected to the ventilator connector 24, the large hollow space of the central bore 22 of the ET adapter may interfere with any waveform measurement performed along the airway, because of the void volume (also known as dead space) formed therein. Furthermore, in the region 30 where the central channel widens from the ET diameter 14 to the ventilation tube connector diameter, which is of similar size to the central bore 22, the abrupt change in diameter causes the formation of eddies in the gas, which destroy the smooth laminar flow, and damage the integrity of the breath waveform. Since this takes place very close to the breath sampling point 39, the sampled waveform is distorted.

In some prior art adapters, an attempt is made to fill this void volume and to eliminate the abrupt diameter change, by means of a second, inner tubular wall 32 protruding from the connector body 24, which fills part of the hollow space inside the ET adapter. However, as previously mentioned, such airway components are typically made as plastic injection moldings, to enable production costs to be kept low. In order to ensure gas tight joins, the components are generally produced with slight tapers, such that one component fits snugly into the other. Because of the inevitable manufacturing tolerances of such plastic parts, and because of the very slight angle of the conical tapers, there may be a wide spread in the closed dimensions of a pair of matching parts when filly mated.

Consequently, the inner tubular wall 32 is often not fully successful in eliminating the void volume, since there will be a space between the outer end 36 of the connector and the inner wall 38 of the ET adapter where the ID increases stepwise, the size of the space depending on how far the ET adapter slides into the ventilating tube connector before making a tight join. The abrupt change in internal diameter of the central bore, and the void volume 30, thus remain. Furthermore, different types of ET adapter have different ID's 20, such that the internal excess space produced circumferencially when the ET adapter and the ventilation tube connector are mated is not always eliminated.

When there is need to monitor the breath of the patient, because of the drawbacks mentioned above of the ET adapter with built-in sampling port, a sampling adapter is often inserted between the ET adapter and the ventilation tube connector. This involves opening the airway connection, with its concomitant disturbance to the patient's respiratory care, and an increased danger of infection.

Figure 2:
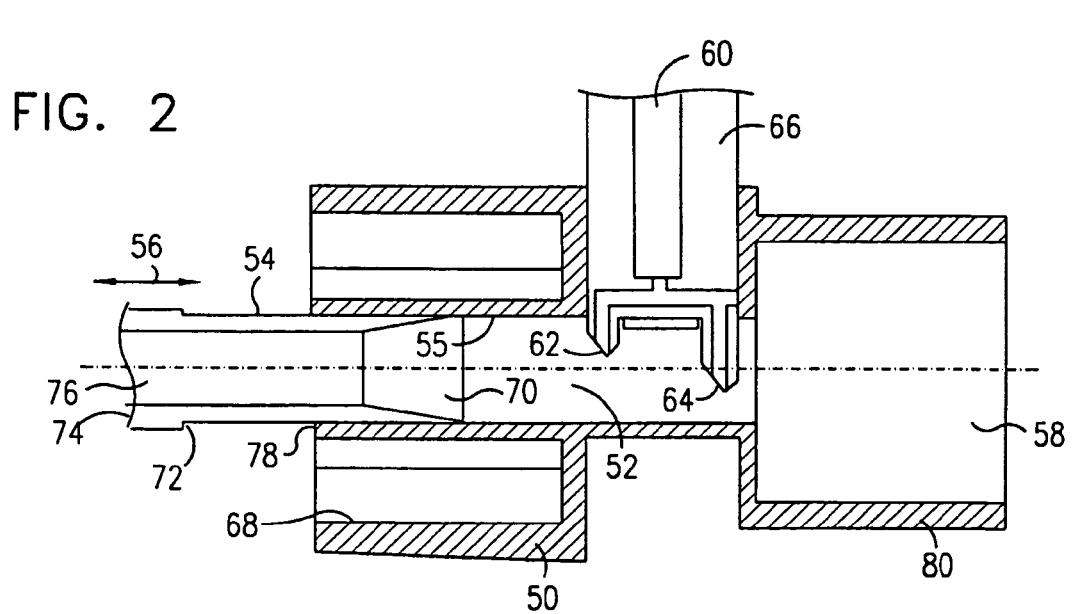
FIG. 2 is a cross-sectional view of a neonatal airway adapter, constructed and operative in accordance with a preferred embodiment of the present invention.

Reference is now made to FIG. 2, which is a cross-sectional view of a neonatal airway adapter 50, constructed and operative in accordance with a preferred embodiment of the present invention. The neonatal airway adapter 50 is inserted between an ET adapter and a ventilation tube connector of a respiratory support and monitoring circuit. The airway adapter 50 is preferably constructed of an injection molded plastic material in the form of a series of tubular sections connected axially, such that the respiratory gases can pass down their length. A central passage 52 preferably has an internal bore of approximately 3.5 mm, this being a suitable internal diameter (ID) for commonly used neonatal ET tubes.

A tubular insert 54 is located inside the central passage 52. The insert 54 can slide in an axial direction 56 with a close fit on the inside wall 55 of the central passage 52 of the airway adapter. An element of friction can be added between the insert 54 and the inside wall 55 of the central passage 52, by means of fine teeth or grooves in the sliding surface of either part, such that the insert essentially remains in the position to which it is slid. The inside bore diameter 76 of the sliding insert 54 is preferably similar or equal to the inside diameter of the narrow tubular bore of ET adapters. At the inner end of the tubular insert 54, the internal passageway opens out into a funnel shaped section 70, such that along the length of the funnel shaped section, the internal diameter 76 of the insert increases from the value it has along the major length of the insert, until at its extremity, it becomes equal to the internal diameter of the central passage 52 of the neonatal airway adapter.

The motion of the tubular insert 54 into the central passage 52 is preferentially limited by an outer end section 74 of slightly increased outer diameter. When the lip of an inner end wall 72 of this increased diameter section abuts on an outer extremity wall 78 of the neonatal airway adapter, the inward motion of the insert is arrested.

The inner surface 68 of the outer wall of the ET end of the neonatal airway adapter has a conical taper, appropriately matched to that provided on the outer wall of ET adapters, designated by dimension 18 in FIG. 1, such that mating of the two forms a gas-tight connection.

The other end 80 of the adapter 50 has a wide bore tubular opening 58, preferentially of similar dimensions to that of the ET adapter shown in FIG. 1, such that a standard ventilator tube connector or a standard flow adapter can be mated with it.

A sampling port arrangement 66 is built into the center section of the neonatal airway adapter to allow attachment of a gas sampling line to convey a sample of the patient's breath to a gas analyzer. The internal bore 60 of the sampling port, according to this preferred embodiment of the present invention, opens into the airway central passage 52 in the form of two small holes 62, 64, supported by the sampling port body structure in the central area of the central passage, away from the walls of the central passage. Their location away from the walls is instrumental in avoiding the ingress into the gas sampling line of secretions and liquids accumulated on the walls of the adapter. The two small holes 62, 64, are located offset from the center line of the central passage, and on either side of the center line, and at different axial positions along the length of the central passage, such that one does not mask the other from the flow of gas along the central passage. Furthermore, two holes are used so that if one hole is blocked by a drop of liquid, held on the end of the hole but not sucked in because of its surface tension, the other hole is available for sampling. Because of the arrangement of the sampling holes, this adapter is known as the Y-Version. The tubular insert 54 is prevented from impacting the sampling port hole structure by means of the above-mentioned lip 72 abutting onto the extremity end wall 78 of the neonatal airway adapter. This prevents damage to the insert during handling before the neonatal airway adapter is assembled in circuit.

Figure 3:
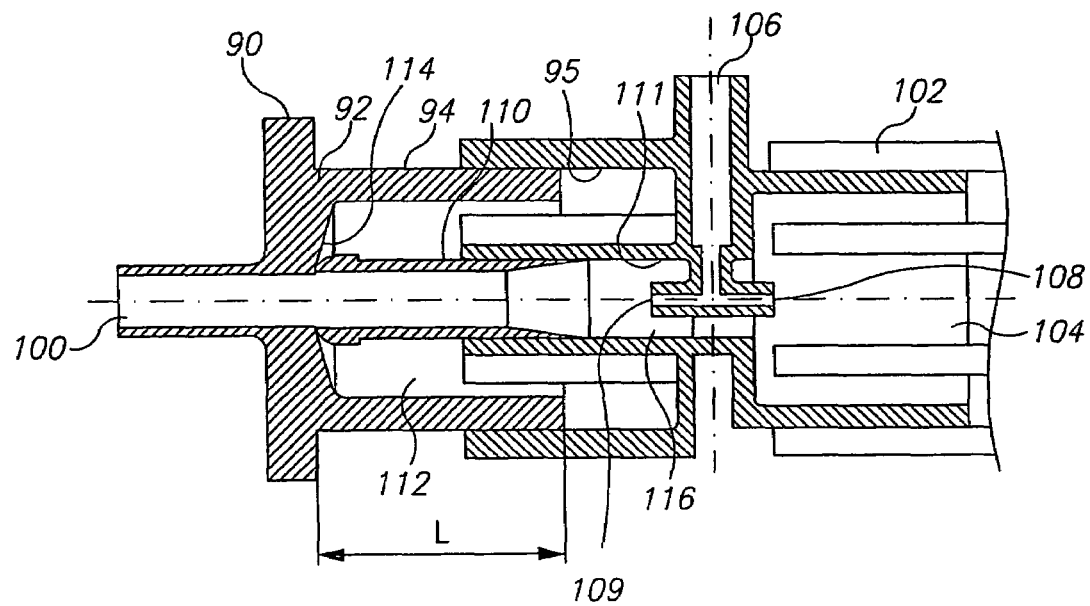
FIG. 3 is a cross-sectional view of a neonatal airway adapter, constructed and operative in accordance with another preferred embodiment of the present invention, having an alternative gas sampling outlet to that shown in FIG. 2, the adapter being shown connecting an ET adapter to a ventilation tube connector.

Reference is now made to FIG. 3, which is a cross-sectional view of a neonatal airway adapter, constructed and operative in accordance with another preferred embodiment of the present invention. In order to show how the adapter interfaces with its associated components in the breathing circuit, it is shown connected between an endotracheal tube adapter 90 and a ventilation tube connector 102. The neonatal airway adapter is packed in such a way that when it is removed from its packaging, the tubular insert 110 is fully extended. It maintains this position during transit and storage by the friction existent between the insert 110 and an inside wall 111 of the central passage 116. As the ET adapter 90 is pushed onto the neonatal airway adapter, an inner wall 114 of the ET adapter where the ID increases stepwise, pushes the insert 110 axially inwards. The ET adapter eventually mates with the neonatal airway adapter, and makes a gas-tight fit by virtue of the conical taper match between the outer surface 94 of the ET adapter wall 92 and the inner bore 95 of the outer wall of the ET-end of the neonatal airway adapter.

It is observed in FIG. 3 that as the insert 110 slides down the central passage 116 of the neonatal airway adapter, a void volume 112 originally in contact with the central passage 116 is now isolated therefrom. When the ET adapter and the neonatal airway adapter finally mate, friction. maintains the insert 110 in the position it has reached, and the patient's breath flows directly from the ET adapter bore 100 into the central passage 116 without contact with this void volume 112. Furthermore, since the internal diameter of the insert 110 is the same as the 3.5 mm. ID bore of the ET adapter passage, the flowing breath does not meet any abrupt bore changes, resulting in the maintenance of smooth laminar flow, with consequential minimal interference to the breath waveform.

The neonatal airway adapter shown has a slightly different sampling port arrangement 106 than that of the embodiment shown in FIG. 2. A pair of sampling holes 108 and 109 are located at opposite ends of a short axial tube centrally located within the central passage. This arrangement has an advantage in that it has lower production costs than that shown in FIG. 2, and has similar advantages in reducing the possibility of the intake of fluids, and in providing a good response time. Because of the arrangement of the sampling holes, this adapter is known as the T-version.

Figure 4:
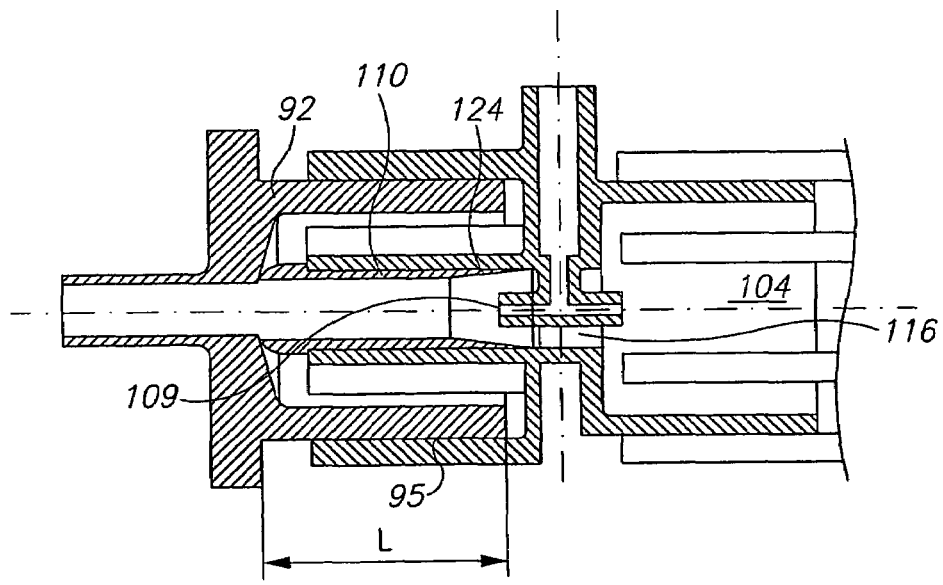
FIG. 4 is a cross-sectional view of a neonatal airway adapter like that shown in FIG. 3 but in a more fully closed position when connected to an ET adapter.

Reference is now made to FIG. 4, which is a cross-sectional view of a neonatal airway adapter of the type shown in FIG. 3, mated with an endotracheal tube adapter and a ventilation tube connector. However, unlike that shown in FIG. 3, the mating position attained by this particular ET adapter and its neonatal airway adapter is such that the closed length of the pair is much shorter. In spite of the large difference in closed length, it is observed that the only difference seen by the gas flow in the central passage is that the flow length is shorter. The insert 110 has simply moved further down the central passage 116, without the introduction of any significant additional void volumes or any bore dimensional changes. This illustrates a major advantage of a neonatal airway adapter according to these preferred embodiments of the present invention, in that it nullifies the effect of the different production-caused, closed lengths of mated component pairs on either side of it in the airway, virtually without any effect on the flow path itself.

The insert 110 has a funnel-shaped section 124 at its inner end. The function of this funnel shaped section 124 is to compensate for the narrowed cross sectional area of the central passage 116 resulting from the presence of the sampling port structure. In the maximum closed position, the sampling hole 109 facing the direction of the patient is located approximately halfway down the funnel of the insert. In this manner, exactly at the sampling point, where maintenance of the waveform integrity is of high importance, the laminar flow of the breath remains reasonably intact, in spite of the perturbations that the sampling hole structure would otherwise have introduced. After the sampling holes, the form of the breath waveform is no longer of importance, and the airway passage widens out into the ventilation tube 104, which has a larger cross section to provide good ventilation conductance.

As an additional consideration, the widened funnel section of the insert is operative to gradually increase the distance of the walls of the central passage of the neonatal airway adapter from the sampling holes. Since secreted liquids and condensed moisture tend to flow along the walls of the central passage, this construction also assists in reducing the undesired ingress of such liquids into the sampling holes.

The length of the funnel-shaped section of the insert is determined by a compromise, determinable by those skilled in the art, between the need to provide a gradual increase in diameter of the bore towards the sampling port, and the need to avoid any unnecessary added volume to the airway passage. Important physical features of the internal bore of the insert are that at the end where it abuts the ET tube, it should preferably have the same ID as that of the ET tube adapter, and at the sampling port end, its ID should be enlarged to provide the above-mentioned compensation.

Figure 5:
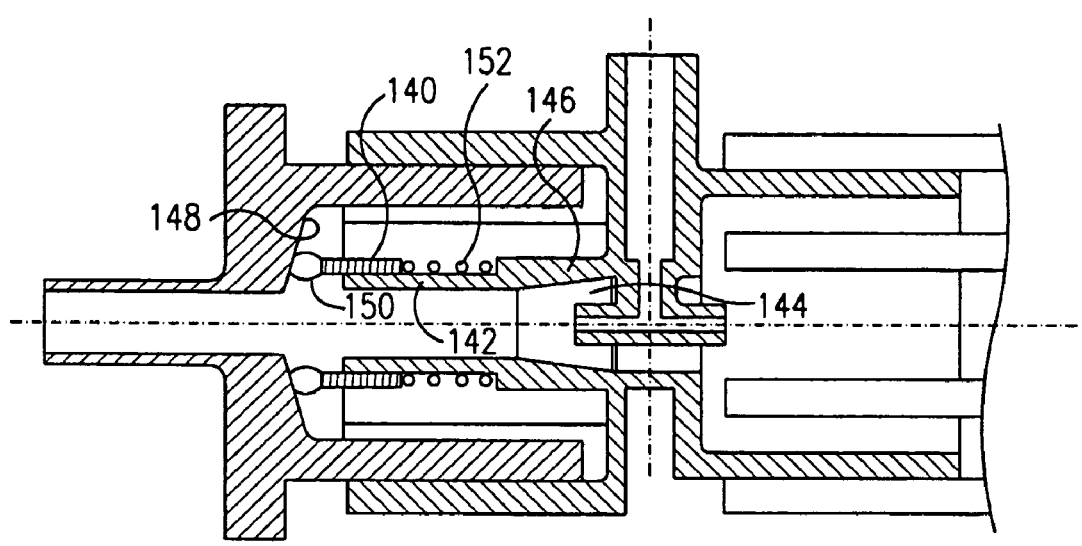
FIG. 5 is a cross-sectional view of a neonatal airway adapter, constructed and operative in accordance with yet another preferred embodiment of the present invention, which uses an alternative method of ensuring a gas-tight seal with the ET adapter to which it is attached.

Reference is now made to FIG. 5 which is a cross-sectional view of a neonatal airway adapter, constructed and operative in accordance with yet another preferred embodiment of the present invention. The overall construction and method of use of this embodiment are similar to those shown in FIGS. 3 and 4. This neonatal airway adapter differs, however, in two aspects:

firstly, it uses a sleeve instead of an insert to ensure an essentially leak-free seal with the ET adapter to which it is attached, and secondly, it uses a spring to ensure positive contact between that sleeve and the ET adapter.

The sleeve 140 in this preferred embodiment slides on the outside of the wall 142 of the central passage of the neonatal airway adapter. The funnel shaped enlargement 144 in the airway bore required opposite the sampling holes is incorporated into the wall 146 of the central passage, and is thus fixed in this position. The sleeve seals against the inner wall 148 of the ET adapter where the ID increases stepwise, preferably by means of a soft elastomer seal 150 with a rounded end attached to the outer end of the sleeve. The seal is maintained in positive contact with the inner wall 148 of the ET adapter, by means of a spring 152 located around the outer wall of the central passage.

The use of a spring has a number of other advantages also. Firstly, it maintains the sleeve in the fully extended position during shipping and handling, until the airway adapter is ready to be attached to its mating ET adapter. The free length of the spring is preferably such that when it is uncompressed, the sleeve remains on the wall of the central passage. Secondly, if for any reason the connection to the ET adapter has to be opened, the spring-loaded sleeve ensures that when reconnected, a positive seal will again be obtained. Finally, the use of a spring to ensure positive motion, assists in overcoming any friction arising from the tight fit required between the parts to ensure gas-tightness. Such friction may otherwise cause sticking of the sleeve to the wall of the central passage.

It is appreciated, though, that the use of the spring is not meant to be an essential part of this preferred embodiment, and that the sleeve may also be preferably utilized without a spring, similarly to the insert in the embodiments shown in FIGS. 2 to 4. Likewise, according to other preferred embodiments, the insert used in the embodiments of FIGS. 2 to 4 may also be used, with suitable structural additions, with a spring, with its incumbent advantages.

The internal diameter of the internal bore of the passage is preferably the same as the internal diameter of the inner bore of the ET adapter, such that there is an approximately smooth-walled transition from the ET-adapter to the passage, thereby endowing this embodiment with the advantages mentioned in this respect in the embodiments shown in FIGS. 2 to 4. The change in diameter at the sleeve location has a minimal effect, both because of the small change in diameter, and because of the small length of sleeve exposed.

Tests performed on neonatal airway adapters constructed according to all of the preferred embodiments of this invention, as shown in FIGS. 2 to 5 indicate that the adapters fulfill the operational requirements for their successful intended use.

Firstly, the adapters connect, without any significant compatibility problems, to all of the most commonly used airway components known to the inventors, including commonly used ET adapters, and the well-known Ballard Closed Suction System, and Bird Flow Adapters.

The void volume is very small, being less than 0.4 cc, and the lengths of the various embodiments of the neonatal airway adapters is also minimal, being 30 mm for the T-version and 36 mm for the Y-version. Because of their small size and aerodynamic internal construction, the pressure drop is minimal, being only an extra 12% when connected to a standard 3.5 mm ET set, and even that low value being obtained at the high airway flow rate of 8 l/min.

The response time of the airway system is hardly affected by the inclusion of the neonatal airway adapter. At a flow rate of 8 l/min, the neonatal airway adapter adds an additional 1 to 3 msec to the response time. At 0.6 l/min, an additional 10 to 13 msec is added. By way of comparison, the commonly used, prior art, RSP adapter adds an additional 43 msec. at 0.6/min. Even if the neonatal airway adapter according to the present invention is not correctly inserted, and the sliding insert is not flush with the inner wall of the ET adapter, the response time is still acceptable. For a 3 mm gap from the inner wall, the added response time has been measured as being only 23 to 36 msec. at a flow rate of 0.6 l/min., which is still less than that of the RSP adapter.

In a test known as the Micro-drop test with Nebulizer, for determining the prevention of liquid entrance into the sampling line, the Y-version allowed entry of 5 ml. of water per hour, and the T-version, only 1 ml. of water per hour. By means of comparison, the RSP adapter allowed entry of 6 ml. of water per hour.

It will be appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An airway adapter comprising:
   a first end section for connecting to an endotracheal tube adapter and extending along a first axis, said first end section having disposed at least partially therein a passage having an internal diameter and extending along a second axis;
   a second end section for connecting to a ventilating tube connector, said second end section being in fluid communication with said passage;
   a breath sampling port in fluid communication with said passage; and
   a generally tubular resiliently extendible passage extension which is coupled to said passage and is retractable axially along said second axis,
   wherein said passage extension retracts axially along said second axis towards said second end section as said airway adapter is pushed onto said endotracheal tube adapter.

2. An airway adapter comprising:
   a first end section for connecting to an endotracheal tube adapter and extending along a first axis, said first end section having disposed at least partially therein a passage having an internal diameter and extending along a second axis, wherein said first and second axes are identical;
   a second end section for connecting to a ventilating tube connector, said second end section being in fluid communication with said passage;
   a breath sampling port in fluid communication with said passage; and
   a generally tubular resiliently extendible passage extension which is coupled to said passage and is retractable axially along said second axis, wherein said passage extension retracts axially along said second axis towards said second end section as said airway adapter is pushed onto said endotracheal tube adapter,
   wherein said endotracheal tube adapter includes a relatively narrow breath passageway which terminates at a breath passageway opening in a wall; and
   said generally tubular resilient extendible passage extension establishes generally sealing engagement with said wall surrounding said breath passageway opening for providing breath communication between said passage and said breath passageway via said extendible passage extension when said airway adapter is pushed onto said endotracheal tube adapter.

3. An airway adapter comprising:
   a first end section for connecting to an endotracheal tube adapter and extending along a first axis, said first end section having disposed partially therein a passage having an internal diameter;
   a second end section for connecting to a ventilating tube connector, said second end section being in fluid communication with said passage;
   a breath sampling port in fluid communication with said passage, said passage extending axially along a second axis away from said second end section beyond said first end section,
   wherein said first and second axes are identical; and
   a generally tubular resiliently extendible passage extension coupled to said passage, axially retractable along said second axis towards said second end section as said airway adapter is pushed onto said endotracheal tube adapter.

4. An airway adapter according to claim 3 wherein:
   said endotracheal tube adapter includes a relatively narrow breath passageway which terminates at a breath passageway opening in a wall; and
   said passage establishes generally sealing engagement with said wall surrounding said breath passageway opening for providing breath communication between said passage and said endotracheal tube adapter when said airway adapter is pushed onto said endotracheal tube adapter.

5. An airway adapter comprising:
   a first end section for connecting to an endotracheal tube adapter, said first end section having disposed partially therein a passage having an internal diameter;
   a second end section for connecting to a ventilating tube connector, said second end section being in fluid communication with said passage; and
   a breath sampling port in fluid communication with said passage, said passage extending away from said second end section beyond said first end section; and
   also including a generally tubular resiliently extendible passage extension coupled to said passage, retractable towards said second end section as said airway adapter is pushed onto said endotracheal tube adapter.

6. An airway adapter comprising:
   a first end section for connecting to an endotracheal tube adapter, wherein said first end section defines a passage;
   a second end section for connecting to a ventilating tube connector in fluid communication with said first end section;
   a breath sampling port in fluid communication with the interior of said endotracheal tube adapter at a location therein upstream of said first end section;
   and also including a generally tubular resiliently extendible passage extension coupled to said passage, axially retractable towards said second end section as said airway adapter is pushed onto said endotracheal tube adapter.

* * * * *